United States Patent [19]

Dutcher

[11] 4,217,913
[45] Aug. 19, 1980

[54] BODY-IMPLANTABLE LEAD WITH PROTECTED, EXTENDABLE TISSUE SECURING MEANS

[75] Inventor: Robert G. Dutcher, Columbia Heights, Minn.

[73] Assignee: Medtronic, Inc., Minneapolis, Minn.

[21] Appl. No.: 6,620

[22] Filed: Jan. 26, 1979

Related U.S. Application Data

[63] Continuation of Ser. No. 839,062, Oct. 10, 1977, abandoned.

[51] Int. Cl.$^3$ .............................................. A61N 1/04
[52] U.S. Cl. ................................. 128/785; 128/419 P
[58] Field of Search .................... 128/419 P, 784, 785, 128/786

[56] References Cited

U.S. PATENT DOCUMENTS

| | | | |
|---|---|---|---|
| 3,198,195 | 8/1965 | Chardack | 128/419 P |
| 3,472,234 | 10/1969 | Tachick | 128/419 P |
| 3,875,947 | 4/1975 | Jula et al. | 128/419 P |
| 3,943,936 | 3/1976 | Rasor et al. | 128/419 P |
| 4,000,745 | 1/1977 | Goldberg | 128/419 P |
| 4,106,512 | 8/1978 | Bisping | 128/419 P |

Primary Examiner—William E. Kamm
Attorney, Agent, or Firm—Hugh D. Jaeger; Joseph F. Breimayer; Lew Schwartz

[57] ABSTRACT

A body-implantable, lead affixed with a pin or pins at its proximal end adapted to be connected to a pulse generator and with an electrode or electrodes at its distal end electrically connected via conductor means and adapted to be securely and permanently attached to a body organ. Electrode means in the form of an elongated member having a circumferential electrode formed on one end thereof and an opening passing therethrough from its proximal to distal end is affixed to the distal end of the conductor means. Tissue securing means are located within a chamber beyond the opening of the electrode body to protect body tissue while the lead is being moved to the desired location. The tissue securing means is then extendable out of the distal end of the electrode means to secure the electrode means in firm engagement with body tissue at the desired location. The lead may be adapted so that the tissue securing means can be automatically actuated to cause the tissue securing means to be secured into the tissue at the desired location in a predetermined manner.

18 Claims, 4 Drawing Figures

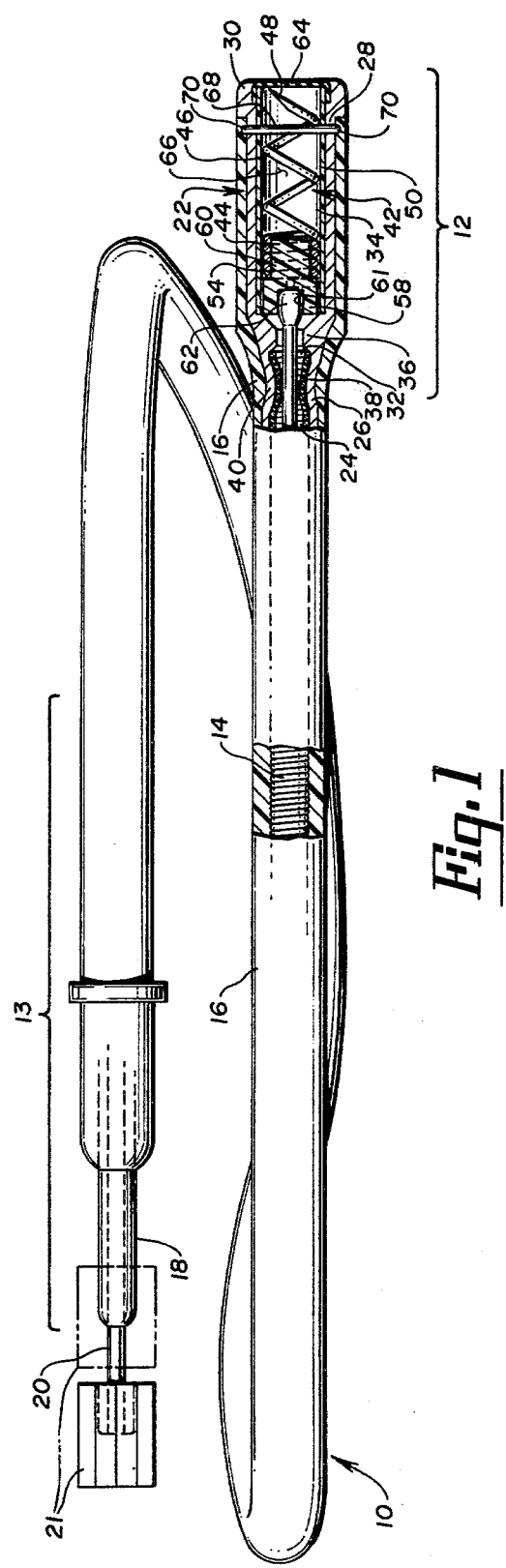

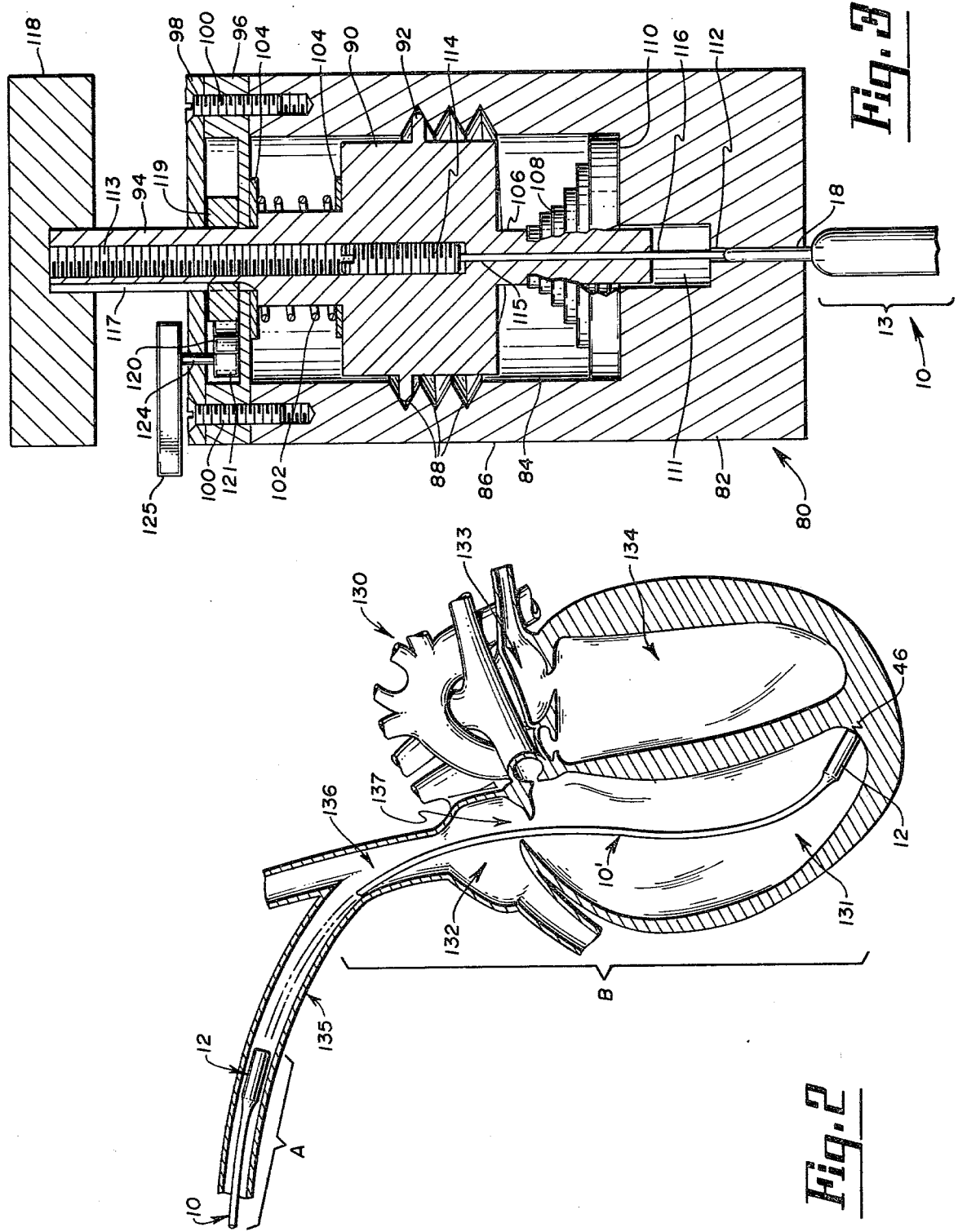

BODY-IMPLANTABLE LEAD WITH PROTECTED, EXTENDABLE TISSUE SECURING MEANS

This is a continuation of application Ser. No. 839,062 filed Oct. 10, 1977, now abandoned.

BACKGROUND OF THE INVENTION

This invention relates to a lead bearing an electrode for electrically connecting an organ inside a living animal body to an electrical device. Notwithstanding its various uses, this invention will be described for purposes of this description for use as an endocardial pacing and sensing lead for connecting an artificial cardiac pacemaker to cardiac tissue.

There are generally two types of body-implantable leads used with cardiac pacemakers—one which requires surgery to expose the myocardial tissue to which the electrode is in some manner or another affixed and another in which a lead with an electrode or electrodes located at its distal end is inserted in and guided through a body vessel such as a vein into the heart where the electrodes contact, and in some cases are secured to the heart through the endothelial tissue lining the inside of the heart. The former leads are generally referred to as myocardial type leads while the latter are generally referred to as endocardial type leads. Examples of prior myocardial leads may be found in U.S. Pat. Nos. 3,216,424; 3,416,534; 3,472,234 and 3,737,579. Examples of prior art endocardial leads may be found in U.S. Pat. Nos. 3,348,548; 3,754,555; 3,814,104; 3,844,292 and 3,974,834 and in publications such as "New Pacemaker Electrodes" by Max Schaldach appearing in Vol. 17 Transactions: American Society for Artificial Internal Organs, 1971, pp. 29-35; German Offenlegungsschrift No. 2,516,848 entitled "Transvenous Stimulation Electrode for Heart Pacemakers" published Oct. 28, 1976; and German Offenlegungsschrift No. 2,539,553 entitled "Electrode Assembly for Medical Purposes" published Mar. 10, 1977. These prior art teachings relate to various types of endocardial leads which are simple to manufacture and importantly are relatively easy to use by the implanting physician. The attributes of an endocardial lead which are most desirable are that the electrode be capable of being firmly secured into the wall of the cardiac tissue to prevent dislodgement while avoiding perforation of the electrode all the way through the cardiac tissue. In addition, it is important that the means used to secure the lead to the cardiac tissue be protected from causing damage to the vein, heart valve, or other tissues through which the lead is inserted into the heart. Other features of importance include electrodes having the desired shape and surface area requirements and means for securing the electrode to the heart without applying any permanent twisting or torque to the lead which will cause it to be stressed while in chronic use. Another problem with prior art leads has been that it is difficult to know exactly to what extent the means for securing the electrode to the cardiac tissue has been successfully achieved when the lead is in its final placement. Still another concern is whether once in place the electrode and/or securing means can be totally withdrawn out of the vein or at least disengaged from cardiac tissue and appropriately repositioned. The above cited prior art references have attempted with varying degrees of success to provide endocardial leads having some of the desirable features without any of the attendant problems or undesirable characteristics as described above.

The body-implantable lead of the present invention provides those features most desirable in an endocardial lead without those undesirable problems or characteristics.

SUMMARY OF THE INVENTION

The above features and advantages of the present invention, as well as others, are accomplished by providing a body-implantable lead comprising electrical conductor means adapted to be connected at its proximal end to a medical device and electrode means affixed to the distal end of the conductor means and adapted to contact tissue inside the body at the desired location. The conductor means and all but an exposed portion of the electrode means are sealed from body fluids and tissue by lead body means of a material substantially inert to body fluids and tissue. The lead body means defines a substantially elongated member having an opening passing therethrough along its length. Tissue securing means are, in a preferred embodiment, located retracted within a chamber therein having an opening at the distal end of the lead body means for preventing injury to the body vessel, valve or other tissues as the lead is inserted and guided through a vessel and for maintaining the electrode means in firm engagement with the tissue when in advanced position at the desired location. Sealing means are provided for preventing entry of body fluids and tissue from reaching the proximal end of the lead through the opening at the distal end of the lead body means.

Preferably, the tissue securing means is a helix having several spaced turns, with a piston member fixed to the proximal end of the helix and positioned in a chamber within the electrode body. A stylet, having a knob at its proximal end that may be pressure fit to the proximal end of the lead passes through the lumen defined by the conductor coil comprising the conductor means. The lumen communicates with the opening in the proximal end of the lead body means such that the distal end of the stylet shaped in the form of a screwdriver head is engageable with a slot in the head of the piston means. When the ring electrode formed at or near the distal end of the electrode body is in firm contact with endocardial tissue at the desired location in the heart, the stylet may be rotated thereby causing the piston means to screw the helix out of the distal end opening in the electrode body and into the endocardial and myocardial tissue to secure and permanently maintain the ring electrode in the desired contact with the tissue. Guide means are provided for ensuring that the helix is properly guided out of the end of the electrode.

In the preferred embodiment the helix is electrically insulated from the electrode so that it serves only to secure the electrode in firm engagement with the tissue but in an alternate embodiment the helix may also be part of the electrode system if desired.

A further feature of the present invention comprises engagement means for engaging said helical tissue securing means and advancing it a predetermined distance into body tissue in a rapid manner, so that it penetrates and attaches to body tissue with reasonable certainty. This is accomplished in a preferred embodiment by spring loading the stylet to ensure that the helix is screwed out of the end of the lead means automatically in both a predetermined manner and amount.

Other features, advantages and objects of the present invention will hereinafter become more fully apparent from the following description of the drawings, which illustrate the invention.

BRIEF DESCRIPTION OF THE DRAWINGS

FIG. 1 shows a view of a preferred embodiment of the body-implantable lead of the present invention including in part an inside elevation partly in longitudinal section of the electrode end portion of the lead;

FIG. 2 shows the lead of FIG. 1 being lodged in and permanently secured to the tissue forming the apex of the right ventricle of the heart;

FIG. 3 shows a sectional view of an alternative stylet mechanism which may be used in conjunction with the lead shown in FIG. 1, and FIG. 4 shows a top view of the mechanism in FIG. 3 with the cover 98 removed.

DESCRIPTION OF THE PREFERRED EMBODIMENT

Referring now to the preferred embodiment of the invention depicted in FIG. 1, there is shown an intravascular endocardial lead comprising an elongated lead 10, a distal electrode end portion 12 and a proximal terminal end portion 13. The lead, in unipolar configuration, comprises a closely wound, coiled conductor 14 in the form of a spring spirally wound about and along the axis of the conductor. The spring coil 14 extends through the length of the lead 10 in a lumen of a jacket or sleeve 16 of electrically insulating material.

The spiral conductor 14 is formed of electrically conductive material offering low electrical resistance and also resistant to corrosion by body fluids. A platinum-iridium alloy is an example of a suitable material. Sleeve 16 is formed of an electrically insulating material, and preferably a silicone rubber such as clean room grade Silastic available from Dow Corning Corporation or a polyether urethane such as Pellethane ® CPR ® 2363-80AE available from the Upjohn Company. These materials are additionally suitable because they are inert and well tolerated by body tissue.

At the proximal end 13 of the lead 10, the conductor 14 as received in and crimped to tubular terminal pin 18. Terminal pin 18 projects beyond sleeve 16 and is adapted for insertion in receptacles provided on the pulse generator, which can comprise any suitable implantable pulse generator such as that shown for example in U.S. Pat. No. 3,057,356.

The pin 18 and the spiral conductor 14 are hollow defining a lumen and thereby adapted to receive a stiffening stylet 20 that extends through the length of the lead 10. The stylet 20 stiffens the lead 10, and its proximal end, adjacent the proximal end 13 of the lead, is formed to provide means, such as the knob 21, which is knurled on its outer surface, for rotating the stylet about its axis to thereby direct the distal end 12 of the lead as it is inserted through the vein. The stylet imparts rigidity to the lead 10 and can be manipulated to introduce an appropriate curvature to the distal, electrode end portion, facilitating the insertion of the lead into and through a vein and through an intracardiac valve, for example one of the jugular veins and the tricuspid valve, to advance the distal end 12 of the lead into the right ventricle of the heart.

At the distal end of the lead 10 an electrode body in the form of an elongated member 22 is provided. Electrode body 22 has an opening 24 which passes completely therethrough along its longitudinal axis from its proximal end 26 to its distal end 28. Integrally formed as part of electrode body 22 and located at its distal end 28 is a raised portion 30 which serves as the ring electrode of lead 10. The outer surface of ring electrode 30 is somewhat rounded and smooth, having the desired shape and surface area for the required stimulation and detection of electrical signals from the heart. Electrode body 22 in the preferred embodiment is a substantially cylindrical member having a circular cross section but may take a number of other configurations. Electrode body 22 preferably is made of a corrosive resistant, electrically conductive material, e.g. platinum or a platinum alloy, a metal oxide or a carbon compound. In the specific embodiment shown, electrode 22 is made of a platinum-iridium alloy. The entire outer surface of electrode body 22 except the raised portion forming ring electrode 30 is insulated as shown by the continuous covering provided by sleeve 16 which conforms to the shape of the outer surface of electrode body 22. In this way the entire lead is electrically insulated when it is connected to the pulse generator from the body except at the ring electrode 30.

Opening 24 passing through electrode body 22 is sectioned into two chambers 32 and 34. Chamber 32 located at the proximal end 26 of electrode body 22 is somewhat smaller in cross section than chamber 34 which is located toward the distal end 28. A restriction 36 is provided on the inner surface of opening 24 and located between the chambers 32 and 34.

Distal end 38 of conductor coil 14 is located in chamber 32 whereby the lumen defined by coil 14 communicates with the very distal end of chamber 32 and with chamber 34 located on the distal side restriction 36. The distal end 38 of coil 14 is physically maintained mechanically and electrically connected to electrode body 22 via a crimped portion 40 in the proximal end 26 of electrode body 22. This mechanical connection between coil 14 and electrode body 22 could be accomplished in ways other than crimping.

Coil 14 is of a well known construction similar to the conductor coils disclosed in U.S. Pat. Nos. 3,348,548 and 3,974,834. A lead such as 10 using a conductor coil such as coil 14 has been shown to be capable of withstanding constant, rapidly repeated flexing over a period of time which can be measured in years. The conductor coil is wound relatively tightly, although there can be a slight space between adjacent turns. This closely coiled construction provides a maximum number of conductor turns per unit length, thereby providing optimum strain distribution. The spirally coiled spring construction of conductor 14 also permits a substantial degree of elongation, within the elastic limits of the material, as well as distribution along the conductor of flexing stresses which otherwise might be concentrated at a particular point. Both the conductor 14 and the insulating sleeve 16 are elastic, and this, together with the coiled construction of the conductor, assures maximum distribution of flexing strains. Conductor 14 may also comprise a multifilar redundant coils of thinner, highly elastic wire.

A tissue securing member in the form of a relatively rigid circular corkscrew or helix 42 is provided having a proximal end 44 of several closely wound turns located in the chamber 34 toward the proximal end thereof. Helix 42 has a distal end 46 formed by about three spaced turns which extend from the closely wound turns of proximal end 44 to the distal end 28 of electrode body 22. These spaced turns end in a point or sharpened tip 48. An insulating hollow sleeve 50 is provided tightly fitting the inner surface of electrode body 22 defining chamber 34. Sleeve 50 may be made of Delrin ® or other suitable body-compatible insulating material. Sleeve 50 serves to electrically insulate helix 42 from electrode body 22 so that helix 42 serves only as a means of securing and maintaining ring electrode 30 in firm engagement with endocardial tissue as will later be described. In this arrangement helix 42 forms no part of the electrode structure. Of course, if it were desired in certain applications that helix 42 forms a part of the electrode structure, this could be accomplished by eliminating insulating sleeve 50 and providing a helix with an outer diameter just slightly smaller than the inside diameter of electrode body 22 defined by the opening. In this way some electrical contact could be provided between electrode body 22, piston 54 and helix 42. Helix 42 in the embodiment shown has a nominal outside diameter of approximately 0.06 inches with the nominal outside diameter of sleeve 16 and ring electrode 30 being about 0.12 inches. Helix 42 is a platinum-iridium coil made of approximately 0.012 inch outer diameter wire.

Also provided in chamber 34 is a member 54 which in the embodiment takes the form of a piston which is generally circular in cross section. Piston 54 may be made of Delrin ® plastic or any other suitable body-compatible material such as a hardened epoxy, nylon or urethane. Piston 54 has a proximal end at which is located a slotted head 58 and a distal end portion 60 which is somewhat smaller in cross-sectional diameter than the head 58. Head 58 has a slot 61 in the proximal end thereof. Distal end portion 60 of piston 54 provides a relatively close fit within the closely wound turns 44 of helix 42. Closely wound turns 44 are secured firmly in head 58 at 60 distally with respect to slot 61. Slot 61 is adapted to receive the distal end of stylet 20 which terminates at its distal end in a screw-driver tip 62. When stylet 20 is fully inserted in through pin 18 and into lead 10 with knob 21 pressure fit on the end of pin 18, the screw-driver tip 62 is firmly seated in slot 61.

In order to seal fluids and body tissue from entering opening 24 through the distal end 28 of electrode body 22, a seal or boot 64, made of a silicone rubber or other suitable body-compatible flexible material is provided. Seal 64 is made to tightly fit opening 24 at the distal end of ring electrode 30. This tight fit may be accomplished, for example, by fitting the seal 64 so that its ends fit tightly between sleeve 50 and the inner wall defined by ring electrode 30 or by fitting tightly in a groove located on the inner wall or surface of ring electrode 30 in opening 24. The seal may be further enhanced by employing a medical adhesive to secure the seal 64 to the electrode body 22. To provide a further seal, if desired, a filler may be provided, for example, as a silicone gel 66 which fills a portion of opening 24 intermediate the distal end of closely wound turns 44 and the most distal ones of spaced turns 46 of helix 42 and surrounds a portion of the spaced turns 46 as shown. Gel 66 may be a Silastic silicon gel which, as helix 42 is screwed distally out of electrode body 22 beyond the distal end of ring electrode 30 by tip 48 piercing seal 64 and spaced turns 46 being screwed out of the distal end of ring electrode 30, moves distally together with the spaced turns 46. Seal 64 forms a seal around the spaced turn 46 which passes through the seal and gel 66 provides a further seal.

To provide a guide to ensure the proper guidance of helix 42 out of the end of ring electrode 30 a monofilament element 68 such as a monofilament nylon thread is provided. Element 68 passes transversely through the outer surfaces of electrode body 22, sleeve 50 and distal end 28 of electrode body 22 just proximal to ring electrode 30. Element 68 is positioned such that it contacts one of spaced turns 46. Element 68 must be made of an electrically insulating material since it contacts both electrode body 22 and helix 42. The ends 70 of element 68 are flared, such as by heat, thereby fixing the element on the outer surface of electrode body 22 in a taut position and preventing the element from being pulled through. As stylet 20 is rotated causing screw-driver tip 62 to rotate piston 54 and accordingly helix 42, the spaced turns 46 contacting element 68 will cause the spaced turns 46 of helix 42 to be properly guided out of the distal end of chamber 34 beyond ring electrode 30.

Turning now to FIG. 2, there is shown an illustration of the partially introduced lead 10 of the present invention in a vein (position A) and the completed introduction and permanent securement of the helix 42 in the tissue forming the apex of the right ventricle of a heart (position B).

In FIG. 2, the heart 130, in cross section comprises the four chambers, namely, the right ventricle 131, the right atrium 132, the left atrium 133 and the left ventricle 134. In the placement of an endocardial lead, it is preferable to use a venous approach on the low pressure side of the heart, that is, through a vein, e.g., the right or left external jugular veins or the right or left cephalic veins 135, the superior vena cava 136, the right atrium 132, the tricuspid valve 137 and the right ventricle 131. During introduction of the lead 10, it must travel a convoluted course through the veins and must pass through the valve 137 without causing any damage to the tissue. It is also desirable that the lead 10 have a small cross section so that it will easily pass through the veins without causing excessive stretching of the veins.

In position A of FIG. 2, the distal end of lead 10 is shown in part. To get to this position stylet 20 is fully inserted in proximal end 13 of lead 10. With knob 21 pressure fit on the end of terminal pin 18. In this position screw-driver tip 62 is seated in slot 61, but helix 42 remains completely within chamber 34 of opening 24. As lead 10 is manipulated and advanced in vein 135, past superior vena cava 136, through atrium 132, tricuspid valve 137 and right ventricle 131 into the apex of the ventricle, since helix 42 remains wholly within chamber 34, it cannot snag the lining of the veins and the valve 37 thereby preventing helix 42 from causing any damage to the body tissue. Likewise, in this condition if the lead 10 is withdrawn, wholly or partially, helix 42 is still within chamber 34 and will not injure the intravascular tissue.

In position B once lead 10 has been properly positioned with ring electrode 30 firmly maintained in contact with cardiac tissue and the appropriate threshhold and R-wave measurements have been taken, knob 21 of stylet 20 is rotated, causing screw-driver tip 62 to cause rotation of piston 54 which in turn rotates helix 42. Element 68 acts to properly guide helix 42 so that tip 48 pierces seal 64 and spaced turns 46 move distally out of the distal end of electrode body 22 beyond ring electrode 30. In this manner the spaced turns 46 are screwed through endocardial tissue into the myocardium. Helix 42 when so screwed into the myocardium serves to secure ring electrode 30 in firm engagement with the tissue to ensure that the proper electrical stimulation and detection of electrical signals will be accomplished through ring electrode 30. To remove the lead 10, stylet knob 21 would be rotated in the opposite direction causing spaced turns 46 to be withdrawn from the tissue. Once helix 42 were positioned wholly within chamber 34 again, then lead 10 could be repositioned and the helix once more screwed out of the end of electrode body 22 into tissue or the lead could be entirely withdrawn out of the heart and back out of vein 135 without helix 42 causing any damage to the body tissue or organs.

The stylet 20 shown in FIGS. 1 and 2 is a simple, manually operated stylet. An alternative to stylet 20 and a further feature of this invention, is to provide a spring-loaded type insertion tool such as 70 shown in cross section in FIG. 3 and in a top view with cover plate 98 removed in FIG. 4. Insertion tool 80 allows helix 42 of lead 10 to be automatically screwed into tissue as will be explained hereinafter. Tool 80 is a substantially cylindrical member which includes a housing 82 having a cavity 84 located in the upper portion thereof defined by a wall 86. Two or three left-handed threads 88 are located in the inner surface of wall 86. A rotor body 90 having a ridge or thread 92 on the outer surface thereof is located within cavity 84 having the same longitudinal axis of rotation along which cavity 84 lies. Rotor body 90 includes a neck 94 which extends out of cavity 84 through a gearing plate 96 and a cover plate 98 covering the top end of housing 82 and secured thereto by screws 100, which pass through cover plate 98, gearing plate 96 and into wall 86.

A compression spring 102 is located around neck 94 and is retained in position between the top end of rotor body 90 and the bottom side of gearing plate 96 by washers 104. Rotor body 90 has a lower extension 106 around which is positioned a constant force spiral spring 108 which rests on the bottom wall 110 of cavity 84 to help maintain extension 106 in proper position. Lower extension 106 of rotor body 90 projects into an opening 111 in the bottom of housing 82. At the bottom of opening 111 is a narrow passage 112 provided to allow the bottom of housing 82 to be pressure fit to pin 18 at the proximal end 13 of lead 10 in FIG. 1.

Rotor body 90 and neck 94 having an opening passing longitudinally and axially therethrough 113 which is threaded to receive a threaded set screw 114 which is threaded down through the top open end of neck 94. At the bottom of threaded opening 113 is a passage 115 having the same longitudinal axis as openings 112 and 113. Passage 115 communicates with opening 111. Set screw 114 has affixed thereto a stylet 116 which passes through passage 115, opening 111, passage 112 and into the lumen defined by the opening in pin 18 and conductor coil 14. Stylet 116 has a screw-driver tip at its distal end the same as tip 62 of stylet 20 in FIG. 1. The neck 94 has a longitudinal slot 117 therein for allowing a ridge (not shown) on the inner surface of a knob 118 to rest so that knob 118 may be used to rotate neck 94 and rotor body 90.

Located on the top surface of gearing plate 96 around neck 94 is an anti-reversing gear 119. Engageable with gear 119 and offset therefrom is an anti-reverse engaging arm 120 which has teeth which are engageable with the teeth on gear 119. Positioned against arm 120 is an anti-reversing cam 121 which is held in position by a cam spring 122 (shown in FIG. 4). Spring 122 is held in place against an inner wall on gearing plate 96. Anti-reverse engaging arm has a hair spring 123 (shown in FIG. 4) which is sprung against an inner wall on gearing plate 96. Arm 120 also has a pivot rod 124 which passes up through cover plate 98 and is fixed to anti-reverse release lever 125.

Insertion tool housing 82, rotor body 90, knob 118 and others of the components of the insertion tool 80 may be made of any suitable materials such as Delrin ® or other hard rubber or plastic body-compatible material.

In operation, tool 80 operates as follows. An ordinary stiffening stylet or stylet 20 of FIG. 1 is inserted into lead 10. The lead 10 is then inserted into and guided into the right ventricle 131 as seen in FIG. 2. This stylet is then totally withdrawn from the lead 10. Prior to the insertion of stylet 116 into lead 10, knob 118 is wound clockwise approximately three turns or until it can no longer be turned. During this winding operation anti-reverse release lever 125 is in its position such that the teeth of anti-reverse engaging arm 120 are engaged with the teeth of anti-reverse gear 119 as seen in FIG. 4 so that the anti-reverse mechanism is in its locked position (i.e. rotor body 90 cannot rotate). Hair spring 123 allows the teeth of arm 120 to ride along the teeth of gear 119 as rotor body 90 is so being wound. After this winding stylet 116 of insertion tool 80 is fully inserted into lead 10 through pin 18 with pin 18 pressure fit into passage 112. The screw-driver tip of stylet 116 rests in slot 61 of head 58 of piston 54. Helix 42 is still in its retracted position wholly within chamber 34. The lead 10 is then positioned appropriately with ring electrode 30 in firm contact with endocardial tissue at the apex of right ventricle 131 and the proper threshold and R-wave measurements are taken at this time to ensure good lead positioning. Lead 10 is then gently pushed forward and the anti-reverse release lever 125 is moved to its unlocked position causing the teeth of anti-reverse engaging arm 120 to become disengaged from the teeth of anti-reverse gear 119. This disengagement will cause rotor body 90 to rotate and unwind approximately three turns. Compression spring 102 aids stylet 116 in its forward rotational movement as rotor body 90 unwinds and also helps prevent backlash of rotor body 90. Cam spring 122 holds cam 121 in its desired locked position during the winding up of rotor body 90 and in its unlocked position during the unwinding. This unwinding causes rotor 90 to rotate thus rotating stylet 116 so that the screw-driver tip 62 rotates piston 54 to cause helix 42 to emerge from chamber 34. Tip 48 pierces seal 64 and spaced turns 46 are screwed approximately three turns into the cardiac tissue. With spaced turns 46 screwed into the tissue, ring electrode 30 is secured in firm engagement with the endocardial tissue in the apex of ventricle 131 or in other suitable sites in the right ventricle or right atrium. It should be understood that although a specific configuration for insertion tool 80 has been described and shown, other configurations for such a tool could be utilized.

In clinically testing leads similar to lead 10 of the present invention, it has been found that the helix 42 can be easily and repeatedly introduced through the vein, through the valve and screwed into the endocardium, unscrewed and withdrawn from the body through the same path without causing any significant damage to the tissue that the lead contacts. The ease of using the lead of the present invention and the positive securement afforded by a corkscrew or helix together with the protective containment of the helix and the positive screw-driver type mechanism for screwing the helix into the tissue make the present invention superior to many prior endocardial lead designs.

Although a unipolar lead design has been illustrated in the description of the preferred embodiment, it will be understood that bipolar leads (that is a lead carrying two electrodes and conductors) may as readily employ the novel electrode design of the present invention. It should be understood that although the use of the lead 10 has been described for use in a cardiac pacing system, lead 10 could as well be applied to other types of body stimulating systems.

It should be further understood, of course, that the foregoing disclosure relates only to the best mode known to the inventor of many possible modes of practicing the invention and that numerous modifications may be made therein without departing from the spirit and scope of the invention as set forth in the appended claims.

What is claimed is:

1. A body-implantable lead adapted to be connected at its proximal end to a medical device and secured at its distal end to tissue of a living body and thereby adapted for electrical stimulation thereof and for detecting electrical signals comprising:
   an electrical conductor extending between the proximal and distal ends of said lead;
   material means substantially inert to body fluids and tissue encasing said conductor;
   an electrode body at the distal end of said lead having electrode means electrically connected to the distal end of said conductor and adapted to supply electrical impulses to and receive electrical signals from tissue at a desired location inside the living body, said electrode body having a chamber therein with an opening in said body;
   helical tissue securing means fitting within said chamber;
   a lumen extending within said material means between the proximal end of said lead and to said chamber; and
   said helical tissue securing means further comprising rotatable means within said chamber adapted to be remotely engaged via said lumen and rotated with respect to said electrical conductor to advance said helical tissue securing means from said enclosed to said extended position beyond said opening.

2. The body-implantable lead of claim 1 further comprising:
   further means extending from the proximal end of said lead to said rotatable means for engaging with and rotating said rotatable means to advance said helical tissue securing means from said retracted position within said chamber to said advanced position and into body tissue to secure said electrode means in contact with body tissue, and wherein said rotatable means further comprise key engagement means for receiving and engaging with said further means.

3. The body-implantable lead of claim 2 wherein said further means further comprise stylet means insertable through said lumen and having key means located at its distal end for engagement with said key engagement means, said stylet means being rotatable from the proximal end of said lead allowing rotation of said rotatable means thereby.

4. The body-implantable lead of claim 3 wherein said stylet means further comprises means at the proximal end of said lead coupled to the proximal end of said stylet means for rapidly rotating said stylet means a predetermined number of turns, whereby said stylet means rapidly rotates said piston means to screw said helical tissue securing means into tissue at the desired location.

5. The body-implantable lead of claim 1 further comprising:
   guide means located in said chamber for properly guiding said helical tissue securing means out of said opening to said extended position.

6. The body-implantable lead of claim 1 further comprising:
   seal means for sealing said chamber from body fluids and tissue of a material through which said tissue securing means may extend in said extended position.

7. The body-implantable lead of claim 1 wherein said electrode means further comprises a cylindrical member having a proximal end and a distal end defining said opening therein, and wherein said material means encases all but at least a portion of said cylindrical member.

8. The body-implantable lead of claim 7 wherein said exposed portion is in the shape of a ring at the distal end of said cylindrical member.

9. The body-implantable lead of claim 1 wherein said tissue securing means is electrically insulated from said electrode means.

10. The body-implantable lead of claim 1 wherein said tissue securing means constitutes said electrode means.

11. A body-implantable lead and stylet assembly having a lead adapted to be connected at its proximal end to a medical device and secured at its distal end to tissue of a living body and thereby adapted for electrical stimulation thereof and for detecting electrical signals, said assembly comprising:
   an electrical conductor extending between the proximal and distal ends of said lead;
   electrode head means affixed to the distal end of said lead having electrode means exposed to body tissue and electrically connected to the distal end of said conductor and adapted to supply electrical impulses to and receive electrical signals from tissue at a desired location inside the living body, said electrode head means having a chamber therein with an opening to body tissue;
   a lumen extending from the proximal end of said lead to said chamber;
   material means substantially inert to body fluids and tissue encasing said conductor and said lumen;
   helical tissue securing means fitting within said chamber and adapted to be screwed into body tissue, said helical tissue securing means further comprising rotatable means within said chamber adapted to be rotated with respect to said electrical conductor to in turn advance said helical tissue securing means from said chamber; and
   stylet means adapted to extend through said lumen and engage with said rotatable means, whereby said rotatable means may be rotated by rotating said stylet means from the proximal end of said lead.

12. The assembly of claim 11 wherein said stylet means further comprises key means at the distal end thereof; and wherein said rotatable means further comprises key engagement means adapted to be engaged by said key means;

whereby said stylet means is engageable with said rotatable means and said tissue means is adapted to be screwed into body tissue by remote rotation of said stylet means from the proximal end of said lead.

13. The assembly of claim 11 wherein said key means comprises the flattened tip of the stylet means and said engagement means comprises a slot in said rotatable means dimensioned to receive said flattened tip.

14. The assembly of claim 11 wherein said stylet means further comprises:

means at the proximal end of said lead coupled to the proximal end of said stylet means for rapidly rotating said stylet means a predetermined number of turns, whereby said stylet means rapidly rotates said piston means to screw said helical tissue securing means into tissue at the desired location.

15. A body-implantable lead assembly, the proximal end of which is adapted to be connected to a stimulator and the distal end of which is adapted to be positioned within the heart, characterized by a helical coil attached to the distal end portion of said lead, and by a bolt which is positioned rearwardly of said coil, is rigidly connected to said coil and has a slot, said coil mounted for screwing into the body tissue from externally by a suitable rotary movement of said bolt relative to said distal and of said lead assembly through a stylet the front portion of which is flattened.

16. The assembly according to claim 15, characterized in that said stylet has a tip is flattened in the manner of a screwdriver.

17. The assembly according to claim 15, characterized in that said coil is rotatably mounted within said lead.

18. The assembly according to claim 15, characterized in that said coil is adapted to be rotatably moved into and out of the lead in the manner of a screw.

* * * * *

UNITED STATES PATENT AND TRADEMARK OFFICE
CERTIFICATE OF CORRECTION

PATENT NO. : 4,217,913
DATED : August 19, 1980
INVENTOR(S) : Robert G. Dutcher

It is certified that error appears in the above–identified patent and that said Letters Patent are hereby corrected as shown below:

Claim 16, line 2, after "tip" insert --which--.

Signed and Sealed this

Twenty-fifth Day of November 1980

[SEAL]

*Attest:*

*Attesting Officer*

SIDNEY A. DIAMOND

*Commissioner of Patents and Trademarks*